United States Patent
Raus (10) Patent No.: US 7,850,694 B2
(45) Date of Patent: Dec. 14, 2010

(54) PNEUMATIC INSTRUMENT FOR TISSUE REMOVAL

(75) Inventor: Laura Raus, Via Principe Eugenio, 23, Rome (IT) 00185

(73) Assignee: Laura Raus, Rome (IT)

( * ) Notice: Subject to any disclaimer, the term of this patent is extended or adjusted under 35 U.S.C. 154(b) by 1279 days.

(21) Appl. No.: 10/551,721

(22) PCT Filed: Apr. 4, 2003

(86) PCT No.: PCT/IT03/00205
§ 371 (c)(1),
(2), (4) Date: Oct. 3, 2005

(87) PCT Pub. No.: WO2004/086988
PCT Pub. Date: Oct. 14, 2004

(65) Prior Publication Data
US 2007/0055217 A1   Mar. 8, 2007

(51) Int. Cl.
*A61B 17/00* (2006.01)

(52) U.S. Cl. .......................... 606/84; 606/170

(58) Field of Classification Search ........... 83/533–537; 606/79–85, 86 R, 87, 167–189; 81/57.19, 81/57.21, 128–129
See application file for complete search history.

(56) References Cited

U.S. PATENT DOCUMENTS

| | | | | |
|---|---|---|---|---|
| 2,625,682 A * | 1/1953 | Cristiano | ........................ | 227/5 |
| 2,740,406 A * | 4/1956 | Tofflemire | .................... | 606/79 |
| 2,751,940 A * | 6/1956 | Miller | ........................ | 30/122 |
| 2,943,524 A * | 7/1960 | Bourne | ........................ | 81/129 |
| 2,948,174 A * | 8/1960 | Bourne | ........................ | 81/129 |
| 3,752,161 A * | 8/1973 | Bent | ........................... | 606/184 |
| 3,913,585 A * | 10/1975 | Wolvek | ........................ | 606/178 |
| 4,174,646 A * | 11/1979 | Kotler | ........................... | 81/128 |
| 4,522,206 A | 6/1985 | Whipple et al. | | |
| 4,530,357 A | 7/1985 | Pawloski et al. | | |
| 4,848,338 A * | 7/1989 | De Satnick et al. | ............ | 606/1 |
| 5,273,519 A * | 12/1993 | Koros et al. | .................... | 606/83 |
| 5,569,258 A * | 10/1996 | Gambale | ........................ | 606/83 |
| 5,700,265 A * | 12/1997 | Romano | ........................ | 606/80 |
| 6,351,659 B1 * | 2/2002 | Vilsmeier | ................... | 600/407 |
| 6,599,291 B1 * | 7/2003 | Foley et al. | ................... | 606/79 |

(Continued)

FOREIGN PATENT DOCUMENTS

DE    3729513    3/1988

(Continued)

OTHER PUBLICATIONS

PCT International Search Report for PCT/IT2003/000205 filed on Apr. 4, 2003 in the name of Fabrizio Caroli.

(Continued)

*Primary Examiner*—Thomas C Barrett
*Assistant Examiner*—Larry E Waggle, Jr.
(74) *Attorney, Agent, or Firm*—Steinfl & Bruno LLP (57) ABSTRACT

Osteotome for the removal of bone and of bone tumors, as well as of ligaments and fibrocartilagineous tissue, during surgery, comprising a pair of blades slidably coupled so that respective distal ends thereof be closable the one against the other for the removal of a bone fragment, pneumatic propelling means for the blades, and a trigger for the operation of the propelling means by a user.

8 Claims, 4 Drawing Sheets

U.S. PATENT DOCUMENTS

| | | | |
|---|---|---|---|
| 2003/0216740 A1* | 11/2003 | Michelson | 606/83 |
| 2003/0225411 A1 | 12/2003 | Miller | |
| 2004/0006335 A1* | 1/2004 | Garrison | 606/27 |
| 2008/0027448 A1* | 1/2008 | Raus et al. | 606/79 |

FOREIGN PATENT DOCUMENTS

| | | |
|---|---|---|
| WO | 02/34144 | 5/2002 |
| WO | 2004/086988 | 10/2004 |

OTHER PUBLICATIONS

PCT International Search Report for PCT/EP2005/010395 filed on Sep. 27, 2005 in the name of Aesculap AG & Co. KG.

PCT International Written Opinion for PCT/EP2005/010395 filed on Sep. 27, 2005 in the name of Aesculap AG & Co. KG.

* cited by examiner fig. 3b fig.5 fig.5b fig.5c ary purposes. It will be made
PNEUMATIC INSTRUMENT FOR TISSUE REMOVAL

FIELD OF THE INVENTION

The present invention relates to a surgical device, and in particular to an osteotome for the removal of bone and of bone tumors, as well as of ligaments and fibrocartilagineous tissue, during surgery, and in particular to an osteotome of the type comprising a pair of blades slidably coupled so as to be closable the one against the other at respective distal ends.

BACKGROUND OF THE INVENTION

Osteotomes for the removal of bone tissue are known, which comprise a pair of parallel blades, the one slidable onto the other so that a bone fragment may be clamped between respective distal ends of the blades themselves and then removed. The sliding of one blade onto the other is generated directly by a surgeon via a handle formed by two rotabably connected levers, each one integral to a respective blade. By forcing said levers the one against the other, the surgeon actually closes the blades.

Such known-art osteotomes also envisage the interposition of an elastic resisting element between said levers, said element being apt to return the latter and therefore the blades integral thereto-to the initial resting position when the surgeon releases the levers themselves.

Over the last five decades, the above described known-art osteotomes have been widely used for surgery requiring the removal of bone tissues, like, e. g. spinal, neurological and orthopedic surgery, ear, nose and throat surgery, maxillofacial and thoracic surgery, and so on.

However, such known-art osteotomes suffer from some relevant drawbacks. In particular, the present invention is based on the observation that such oseotomes, in order to be operated and to produce the removal of a bone fragment, require the exertion of a remarkable force by the surgeon, also due to the fact that the latter should overcome the resistive force of said resisting element. As surgery generally requires a continuous and repeated use of the osteotome, the operation modes of the known-art osteotomes tire the surgeon, and in particular the osteotome-operating limb. Moreover, in the effort of operating the osteotome, the surgeon could impart undesired swinging motions thereto. All of this affects surgery accuracy and safety, and prolongs the related times.

SUMMARY OF THE INVENTION

Hence, the technical problem underlying the present invention is that of providing a surgical device, and in particular an osteotome, allowing to overcome the drawbacks mentioned hereto with reference to the known art. Such a problem is solved by a surgical device according to claim 1.

According to the same inventive concept, the present invention further relates to a surgery kit according to claim 24.

The invention further provides a surgery apparatus according to claim 26. Preferred features of the present invention are provided in the dependent claims thereof.

The present invention provides some relevant advantages. The main advantage lies in the fact that the surgical procedure is optimized in terms of accuracy, safety and times. In fact, the presence of propelling means for the slidable blade interposed between the latter and suitable operation means apt to be handled by the user dispenses the surgeon from directly providing the operating force of the osteotome blades. Hence, during surgery the operator's attention may entirely focus on the structures to be removed.

BRIEF DESCRIPTION OF THE DRAWINGS

Other advantages, features and the modes of employ of the present invention will be made apparent in the detailed description of some embodiments thereof, given by way of example and not for limitative purposes. It will be made reference to the figures of the annexed drawings, wherein.

DETAILED DESCRIPTION

Figures 1, 2:
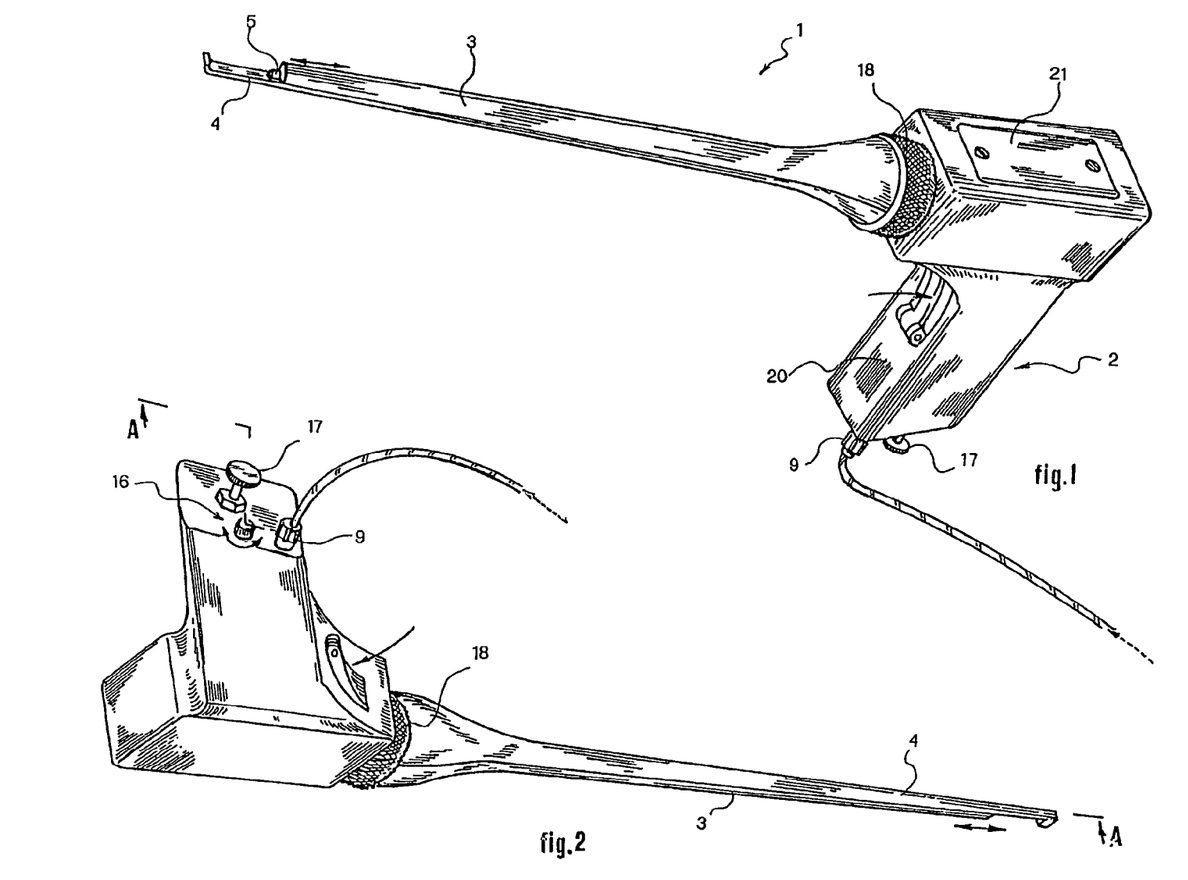
FIG. 1 shows a top perspective view of an embodiment of the osteotome according to the present invention.
FIG. 2 shows a bottom perspective view of the osteotome of FIG. 1.

Referring initially to FIG. 1, an osteotome according to an embodiment of the invention is generally indicated by 1.

The osteotome 1 comprises a main body 2—or handpiece—apt to be handled by a user, and a pair of blades, and specifically a first blade 3 and a second blade 4, which in the present embodiment are removably connected to the main body 2 according to modes that will be illustrated later on.

The main body 2, serving as chassis of the osteotome 1, comprises a portion 20 apt to be bandied by the surgeon by a single hand; the other hand may be used to hold the blades during surgery.

The main body 2 further provides a top closure panel 21 to allow access to components internal thereto.

The blades 3 and 4 are located parallel and side-by-side and are slidably coupled the one to the other, as in known art osteotomes.

Figures 3, 3A, 4A, 4B:
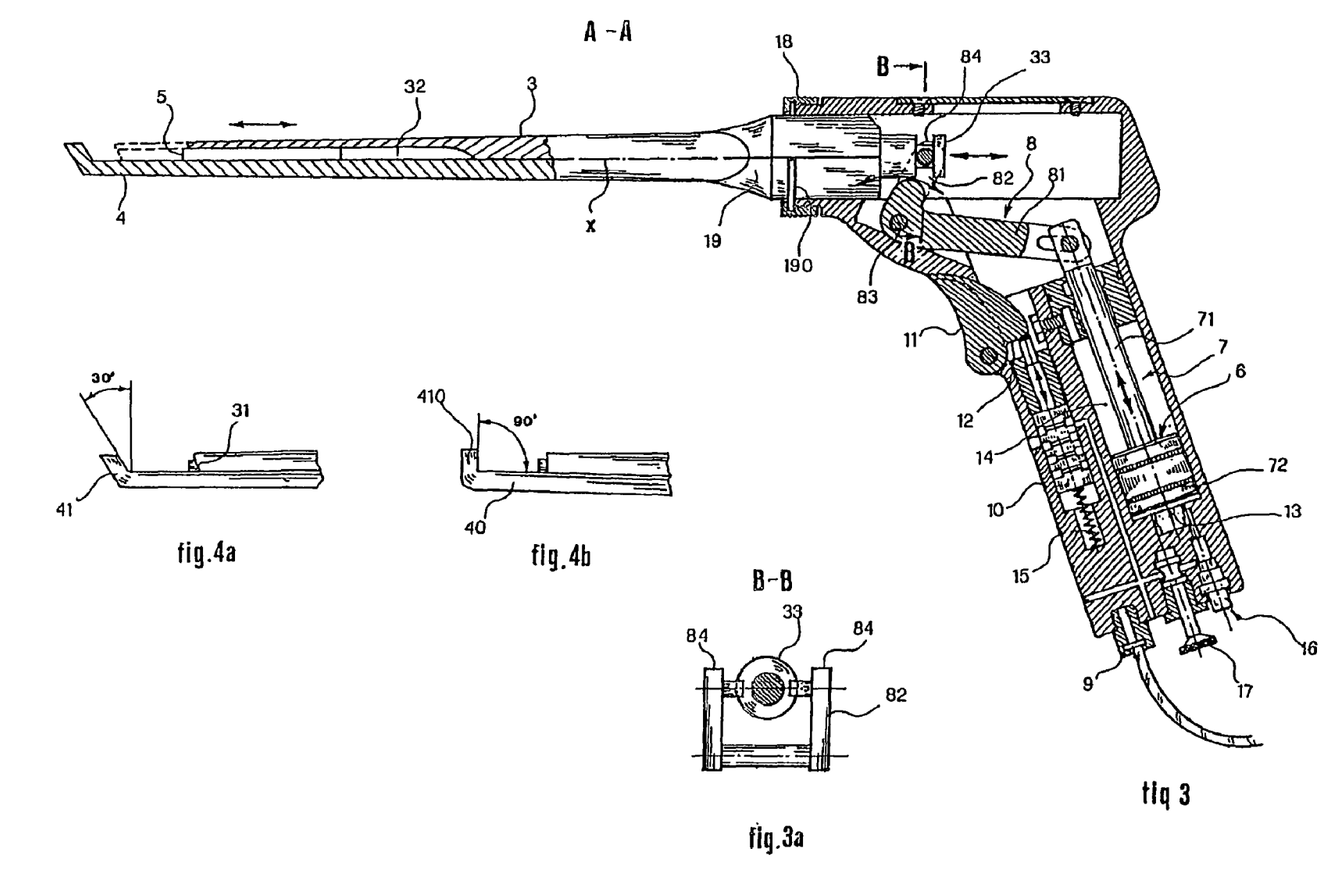
FIG. 3 shows a longitudinal sectional view of the osteotome of FIG. 1.
FIG. 3A shows a cross sectional view of the osteotome of FIG. 1, taken along line B-B of FIG. 3.
FIGS. 4A and 4B each show a side view of a detail of the blades of the osteotome of FIG. 1 and of a variant of such detail, respectively.

As it is shown in greater detail in FIG. 4, and always as in known-art osteotomes, such blades 3 and 4 have respective cutting distal ends, indicated by 31 and 41, respectively, mutually closable the one against the other for the removal of a bone fragment or other biological material during surgery. For this purpose, the second blade 4 has, at the end 41, a slant with respect to the predominant direction of development of the blades themselves. In particular, in FIG. 4A there has been depicted a blade 4 having, at the distal end 41, a slant of about 30 degrees with respect to the vertical.

However, a person skilled in the art will understand that the invention is fit to be used in association with blades having any tilt whatsoever. For example, as it is shown in FIG. 4B, the invention may be associated with a second blade 40 the distal end 410 of which has a tilt of about 90° with respect to the horizontal.

Referring now to FIG. 3, in order to produce said closing of the blades 3 and 4, as already mentioned above the first blade 3 is slidable onto the second blade 4. The first blade 3 has a longitudinal groove 32 faced onto the second blade 4 for allowing the parallel sliding between the two blades. In order to prevent bone fragment entrapment within such groove 32, i.e. between the blades 3 and 4, an elongate element 5 is longitudinally secured onto the second blade 4. When the first blade 3 is moved backward with respect to the second blade 4, this element 5 prevents dragging of the bone fragment by the first blade itself.

The main body 2 internally houses propelling means for the first blade 3, globally indicated by 6 and apt to determine the sliding of the latter with respect to the second blade 4.

In the present embodiment, the propelling means 6 is of pneumatic type. In particular, it comprises a cylinder-piston system 7 and a motion transmission member 8 rotatably coupled to the stem 71 of said piston at respective ends.

In the present embodiment, the transmission member 8 is substantially L-shaped, comprising in particular a first arm 81, which is rotatably connected to the stem 71 at a free end thereof, and a second arm 82 integral to the first arm 81 and rotatably connected, at the end of the member 8 opposed to that connected to the stem 71, to the first blade 3. The specific connection modes between the member 8 and the first blade 3 provided in the present embodiment will be detailed hereinafter.

Moreover, the transmission member 8 is hinged to the main body 2 at a central region thereof of intersection of said arms 81 and 82 by a fulcrum element 83. Therefore, the transmission member 8 forms a sort of first class lever whose motive force is that exerted by the piston and whose resistive force is that associated with the first blade 3 and the bone fragment entrapped between the blades 3 and 4. In order to attain an advantageous motive force/resistive force ratio, the first arm 81 is longer than the second arm 82 and preferably in a 3:1 ratio therewith.

The pneumatic propelling means 6 further comprises an intake 9, in form of pipe holder, for supplying compressed air from the outside, and in particular for connecting the osteotome 1 to the pneumatic system of the operating theatre.

Therefore, the propelling means 6 comprises a pneumatic circuit interposed between said intake 9 and said cylinder-piston system 7 for the controlled supplying of compressed air at both sides of the piston body 72.

Said pneumatic circuit is implementable with known components and modes, and in particular it comprises a compressed air supply channel network and an associated one- or plural-way valve system. In the section of FIG. 3, only a few of the channels and of the other components of such circuit are visible. Instead, a schematic global depiction of the circuit itself is shown in FIG. 3B.

Figure 3B:
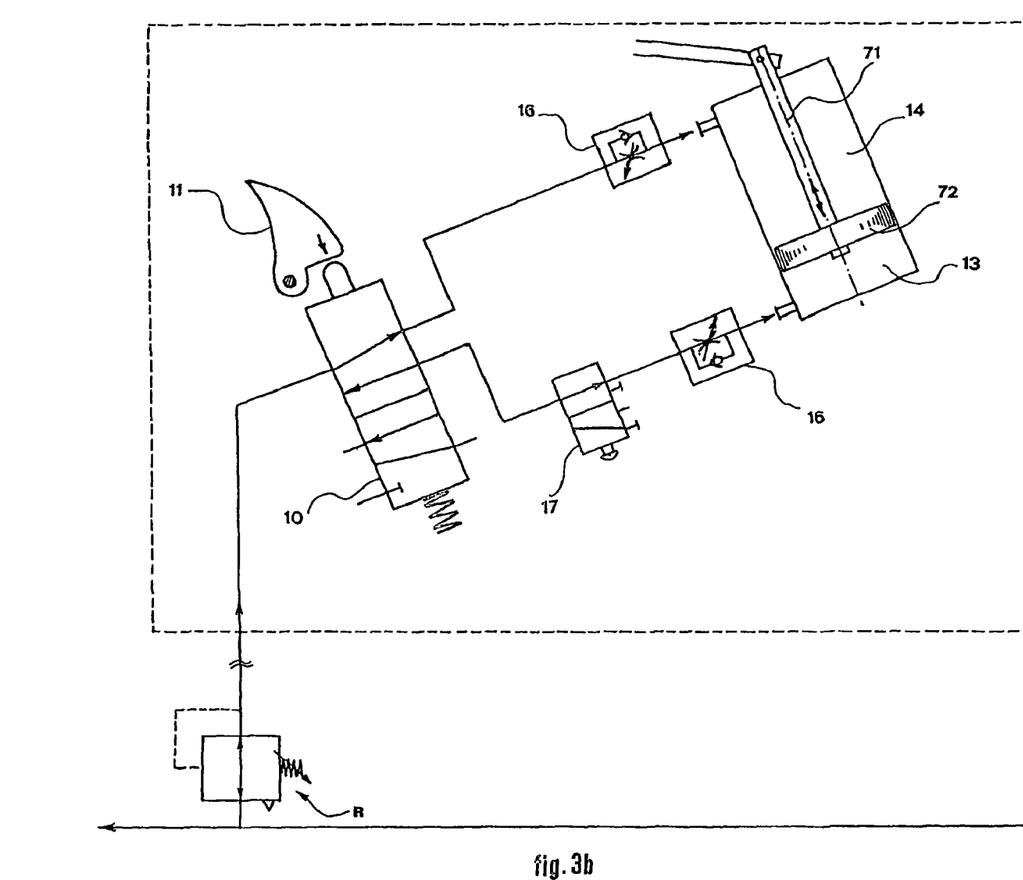
FIG. 3B shows a schematic representation of a portion of a pneumatic circuit of the osteotome of FIG. 1.

Hence, with reference to FIGS. 3 and 3B, said pneumatic circuit comprises a plural-way valve 10. The latter directly cooperates with an operation trigger or push button 11, located at the portion 20 of the main body 2 and apt to be handled by the surgeon for determining the operation of the propelling means 6 and therefore the closing of the first blade 3 onto the second blade 4.

The overall arrangement is such that, when the user presses the trigger 11, the latter, insisting with one surface 12 thereof onto the body of the valve 10, determines the lowering of said valve body and the entailed compressed air supplying to a cylinder region 13 located below the piston body 72. Concomitantly, there is allowed the outlet of air from the cylinder region 14 located above the piston body 72. Then, the air inflow in the bottom region 13 determines the upward motion of the piston, i.e. its motion towards the transmission member 8. The latter, by effect of said piston motion, is induced in rotary motion, as it is indicated by the arrow of FIG. 3, thereby determining the advance of the first blade 3 with respect to the second blade 4.

When the surgeon releases the trigger 11, a mechanism specular to the above-described one is determined. In particular, an elastic resisting member 15 automatically returns the body of the valve 10 to the initial position, determining an inflow of air to the cylinder top region 14 and an outflow of the air contained in the bottom region 13.

Hence, it will presently be appreciated that in order to produce the motion of the top blade 3 the surgeon should merely apply a light force onto the trigger or push button 11 in order to overcome the resistive force of the elastic element 15. The operation via a trigger or equivalent system, requiring a minimal force, causes no undesired motions or swinging of the entire osteotome, as instead occurring in known-art systems. Moreover, there are no problems of the osteotome interfering with other instruments or elements in the surgical field, like e. g. self-retaining retractors.

As illustrated hereto, the propelling means 6 is operable by a user via said trigger 11. The overall configuration of the described pneumatic system is such that, according to the speed at which the surgeon presses onto the trigger 11, there is attained an adjustment of the advance speed of the first blade 3 with respect to the second blade 4, osteotomic force exerted onto the material to be removed being equal. Therefore, the system of the invention enables to adjust the blade-sliding speed with no concomitant osteotomic power loss.

Of course, variant embodiments can provide operation means differing from said trigger 11.

Always with reference to FIGS. 3 and 3B, the osteotome 6 further comprises means 16 for adjusting the closing speed of the blades 3 and 4, which in the present embodiment is implemented by a flow regulator operable at the base of the main body 2 and partially visible also in FIG. 2. This flow regulator 16 is apt to control the flow resistance at the pneumatic circuit portion associated with the cylinder bottom region 13.

It will be appreciated that the hereto-introduced adjusting means is particularly useful for the adaptability of the instrument to osteotomic blades of different size. Moreover, also this means allows an adjusting of the advance rate of the first blade 3 with respect to the second blade 4, osteotomic force being equal.

Moreover as it is schematically shown in FIG. 3B, the osteotome 1 may further allow an adjustment of the closing force of the blades 3 and 4 by a pressure regulator R located externally thereto and incorporated in the pneumatic system of the operating theatre.

Of course, variant embodiments may envisage implementation modes of the rate and/or of the closing force of the osteotome blades alternative to the above described ones.

In the present embodiment, the osteotome 1 also comprises means 17 for inhibiting operaton of the propelling means 6. In the present example, such means 17 comprises a block valve, it also indicated by 17, apt to deny the pneumatic circuit portion associated with the cylinder bottom region 13. The means 17 are operable by the surgeon, e. g. via a simple push button mechanism located at the base of the main body 2, in order to allow a safe pass of the osteotome to other operators, e. g. to a medical assistant. In fact, when such means 17 is inserted there is no risk that the assistant, accidentally pressing the trigger 11 while cleaning the blades 3 and 4, be wounded due to the abrupt closing thereof.

Hereinafter, with reference to FIGS. 3 and 3A, there will be detailed the modes of connecting the first blade 3 to the second arm 82 of the element 8.

In the present embodiment, the arm 82 ends in a substantially U-shaped end 84, which is apt to removably and rotatably receive a knob-shaped proximal end 33 of the first blade 3. In particular, with reference to the configuration of FIG. 3, the first blade 3 can rotate within the U-shaped portion 84, and therefore with respect to the transmission member 8, about an axis of rotation X parallel to the blade itself. Moreover, always with reference to the configuration of FIG. 3, the first blade 3 may be disconnected from the element 8 by a mere downward extracting motion apt to disengage the portion 84 from the portion 33.

Figure 5:
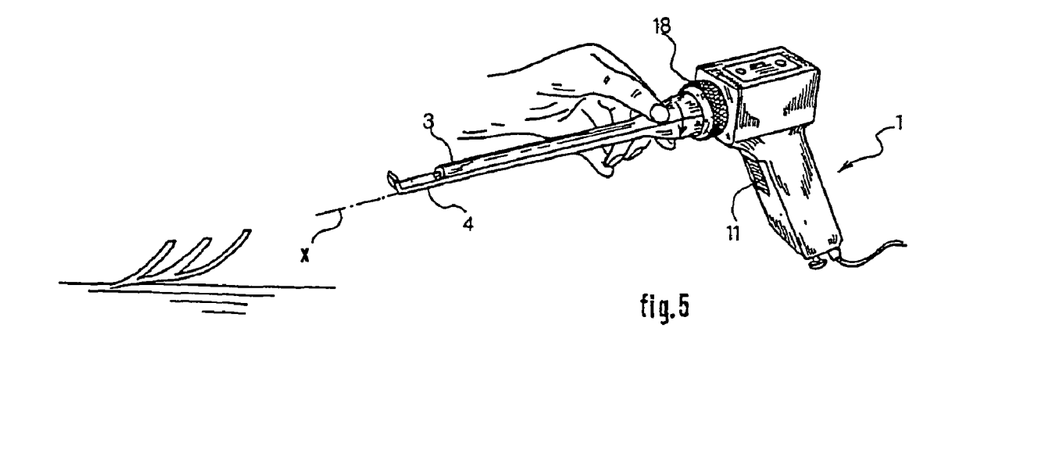
FIGS. 5A to 5C illustrate the modes of employ of the osteotome of FIG. 1, each showing a perspective view thereof during use in surgery.
Figure 5B:
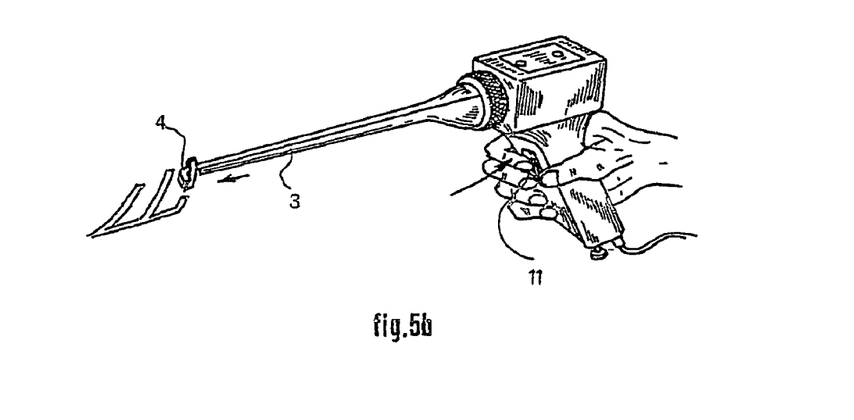

As it is shown always in FIG. 3, and also with reference to FIGS. 5A and 5B, the removable connection of the blades 3 and 4 to the main body 2—and then, in short, to the propelling means 6—is further entrusted to a ring nut 18 apt to be screwed at a threaded end face of the main body 2 itself. This ring nut 18 cooperates with a sleeve 19 for retaining the blades 3 and 4 so as to block the latter with the main body 2. In particular, the first blade 3 is slidable within the sleeve 19 so as to be connectible to the transmission member 8 in the abovedescribed manner. The second blade 4 is instead integral to the sleeve 19 and it is apt to be blocked with the ring nut 18 by a tooth 190.

According to the hereto-described arrangement, when the ring nut 18 is firmly tightened onto the main body 2, the sole relative degree of freedom between the latter and the blades 3 and 4 is that associated with the sliding of the first blade 3 onto the second blade 4. However, as it is shown in FIG. 5B, it suffices to slightly loosen the ring nut 18 with respect to the main body 2 in order to allow the blades 3 and 4 to rotate integrally the one to the other with respect to the main body 2 about said axis of rotation X substantially parallel to the blades themselves. Thus, the osteotomic blades may be rotated on a continuous 360 degrees field.

This aspect of the invention, i.e. the fact that the blades 3 and 4 are rotatable with respect to the main body 2, allows the operator to keep the latter—and therefore the hand holding and operating the instrument—always in the most suitable and comfortable position, and to position the osteotomic blades 3 and 4 with any working angle in the 360 degrees with respect to the body 2. This constitutes a relevant advantage with respect to the known-art systems, in which the operator is instead forced to rotate the entire instrument to arrange the blades in a desired angle, or even to change several instruments during the same surgery, each instrument being preset with blades having a fixed angle with respect to the operation levers.

It will further be appreciated that the removable connection between blades 3 and 4 and main body 2 and the heretodescribed modes of such connection allow the operator to easily interchange the pair of blades connected to the main body, so as to always use the blades most suitable for the specific surgery to be carried out. In particular, the change of the pair of blades can take place with a few simple motions, i.e.: rotating the ring nut 18; pressing the trigger 11 to produce an advance of the member 8 and therefore of the blade 3 connected thereto; and disengaging the connection between the knob portion 33 of the blade 3 and the U-shaped end 84 of the second arm 82. Then, with reversed motions, the connection of the new pair of blades is attained.

Hence, the osteotome of the invention may also be provided in form of surgery kit, such a kit comprising said main body 2 apt to be handled by a surgeon and a plurality of pairs of osteotomic blades removably connectable thereto, i.e. to the propelling means for the slidable blade.

Such a provision in form of kit also entails the advantage of smaller dimensions of the entire assembly on operating tables as well as in sterilization baskets with respect to the traditional osteotomes, in which to each blade type there correspond an entire different instrument.

Moreover, the removable connection between the main body—and therefore the propelling means—and the blades also entails the advantage of requiring no disassembly or replacement of the entire instrument when the blades deform or wear out.

By now, the modes of employ of the osteotome 1 will have been made apparent, and will only briefly be recalled herein.

The surgeon can select and rapidly mount the osteotomic blades 3 and 4 that are most suitable for the surgery or surgery step to be carried out onto the main body 2 according to the modes described above.

Then, previously to the blade mounting, the osteotome 1 is connected to the pneumatic system of the operating theatre via the intake 9.

Figure 5C:
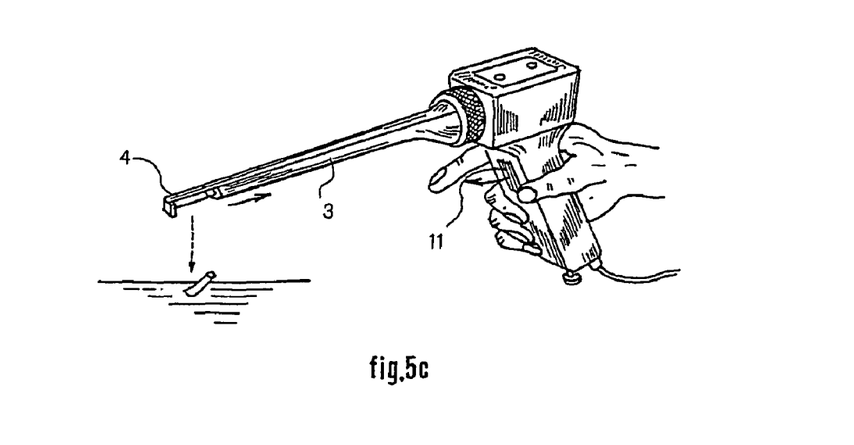

At this point, as it is shown in FIGS. 5A to 5C, the surgeon may operate—easily and with a negligible force—the propelling means 6 via the trigger 11 and remove the desired tissue portions O.

During surgery, it is also possible to rotate the blades 3 and 4 with respect to the handle 20, to adjust the blade operating rate by the trigger 11 itself or by the means 16, or even to adjust the closing force by the regulator R, according to the modes already illustrated hereto.

Moreover, when the osteotome 1 is passed to an assistant, or anyhow when it is not to be used, there may be inserted the inhibiting means 17 for ensuring operator's safety.

By now, it will be better appreciated that the device of the invention allows to improve the accuracy of surgery.

In fact, first of all, as already hinted above, the surgeon may concentrate onto the action of the blades instead of being diverted by the need to directly operate them through levers. The involvement of the surgeon's cerebral cortex, and in particular of the premotor gyrus, is near-negligible, consisting of the repeated pressure of the sole trigger 11, whereas the visual cortex is involved in an exclusive and prominent manner to the end of recognizing the structures involved in the osteotomic act (e.g.: radicular cysts, dural casing, peridural venous sinuses, cranial base vascular and nervous structures, etc.).

It will also be appreciated that the device of the invention, by providing propelling means for the blades and operation means for the latter, rather than a direct operation of the blades by a user, increases and steadies the closing force of the osteotomic blades, regardless from the extent of the force applied onto the trigger by the operator carrying out the surgery.

Moreover, the provision of suitable operation means 11 for the propelling means 6 allows to slow down or instantaneously stop the operation of the blades—by a lower pressure or the release of the trigger—when an interposition of structures not destined to be removed is suspected. In these cases, the reaction times of the surgeon and of the instrument are markedly reduced with respect to the conventional systems requiring a manual operation of the blades.

Furthermore, the osteotome is less bulky than the known art systems, which are bound to the bulkiness associated with the opening of the operation levers. This prevents the occurrence of the abovementioned problems of interference of the osteotome with other instruments or elements in the surgical field.

Moreover, in known-art systems the need to grasp in one hand the blades wide apart is another relevant drawback, since such a holding is cumbersome for a small-handed surgeon. Evidently, this drawback as well is overcome by the osteotome of the invention, in which the main body may have a reduced-size holding portion.

Moreover, it will be appreciated that the pneumatic implementation of the propelling means as above is easy, cost-effective and perfectly compatible with the structures already present in the operating theatre. Furthermore, such implementation requires no lubrication systems possibly incompatible with operating room sterility requirements. Additionally, pneumatic propelling is perfectly and immediately compatible with the required blade closing forces and speeds.

It will be understood that the present invention is susceptible of several embodiments and variant embodiments alternative to those described hereto.

For example, the osteotome of the invention may provide means for coupling to or for cooperating with a neuronavigation system, e.g. one or more position sensors, and hence be employed in the context of a surgery apparatus comprising said neuronaviqation system. This allows a mapping of the bone to be removed, and therefore the real-time assessment of the work already carried out and to be carried out, optionally with a three-dimensional virtual representation of the anatomic structures to be preserved, studied with MR, TC, and scopy. Embodiment variants could also provide an integration with robotized systems apt to automatically carry out some repetitive and pre-codified surgical procedures.

The present invention has been hereto described with reference to preferred embodiments thereof. It is understood that other embodiments may exist, all falling within the concept of the same invention, and all comprised within the protective scope of the claims hereinafter.

The invention claimed is:

1. A surgery kit, comprising a surgical device, the surgical device being adapted to remove bone, cartilaginous and the like tissues during surgery, the surgical device comprising:
   a pair of side-by-side blades, slidably coupled so that respective distal ends thereof be closable the one against the other for the removal of a tissue fragment;
   propelling means, connected or connectible to a slidable blade of said pair and apt to determine the sliding thereof with respect to the other of said blades, said propelling means being pneumatic propelling means and comprising a piston having a stem apt to produce sliding of the slidable blade of said pair;
   operation means for the operation of said propelling means by a user; and
   a main body apt to be handled by a user and connected or connectible to said pair of blades, said main body comprising a portion apt to be handled by the user by a single hand, said operation means being located at said portion,
   wherein said piston is coupled to said slidable blade by interposition of a motion transmission member, said motion transmission member being a lever rotatably connected at opposed ends thereof to said slidable blade and to the stem of said piston, respectively, the lever being further connected to a chassis of the surgical device at a central position thereof,
   the surgery kit further comprising a plurality of osteotomy blades removably connectible to said propelling means.

2. A surgery apparatus, comprising a surgical device apt to the removal of bone, cartilaginous and the like tissues during surgery, the surgical device comprising:
   a pair of side-by-side blades, slidably coupled so that respective distal ends thereof be closable the one against the other for the removal of a tissue fragment;
   propelling means, connected or connectible to a slidable blade of said pair and apt to determine the sliding thereof with respect to the other of said blades, said propelling means being pneumatic propelling means and comprising a piston having a stem apt to produce sliding of the slidable blade of said pair;
   operation means for the operation of said propelling means by a user; and
   a main body apt to be handled by a user and connected or connectible to said pair of blades, said main body comprising a portion apt to be handled by the user by a single hand, said operation means being located at said portion,
   wherein said piston is coupled to said slidable blade by interposition of a motion transmission member, said motion transmission member being a lever rotatably connected at opposed ends thereof to said slidable blade and to the stem of said piston, respectively, the lever being further connected to a chassis of the surgical device at a central position thereof,
   the surgery apparatus further comprising a neuro-navigation system associated to the surgical device.

3. A surgical device apt to the removal of bone, cartilaginous and the like tissues during surgery, comprising:
   a pair of side-by-side blades, slidably coupled so that respective distal ends thereof be closable the one against the other for the removal of a tissue fragment;
   propelling means, connected or connectible to a slidable blade of said pair and apt to determine the sliding thereof with respect to the other of said blades, said propelling means being pneumatic propelling means and comprising a piston having a stem apt to produce sliding of the slidable blade of said pair;
   operation means for the operation of said propelling means by a user; and
   a main body apt to be handled by a user and connected or connectible to said pair of blades, said main body comprising a portion apt to be handled by the user by a single hand, said operation means being located at said portion,
   wherein said piston is coupled to said slidable blade by interposition of a motion transmission member, said motion transmission member being a lever rotatably connected at opposed ends thereof to said slidable blade and to the stem of said piston, respectively, the lever being further connected to a chassis of the surgical device at a central position thereof, and
   wherein the arrangement is such that the blades of said pair can rotate with respect to said operation means, during surgery, about an axis of rotation substantially parallel to the blades themselves.

4. A surgical device apt to the removal of bone, cartilaginous and the like tissues during surgery, comprising:
   a pair of side-by-side blades, slidably coupled so that respective distal ends thereof be closable the one against the other for the removal of a tissue fragment;
   propelling means, connected or connectible to a slidable blade of said pair and apt to determine the sliding thereof with respect to the other of said blades, said propelling means being pneumatic propelling means and comprising a piston having a stem apt to produce sliding of the slidable blade of said pair;
   operation means for the operation of said propelling means by a user; and
   a main body apt to be handled by a user and connected or connectible to said pair of blades, said main body comprising a portion apt to be handled by the user by a single hand, said operation means being located at said portion,
   wherein the blades of said pair of blades are removably connected or connectible to said main body,
   wherein said piston is coupled to said slidable blade by interposition of a motion transmission member, said motion transmission member being a lever rotatably connected at opposed ends thereof to said slidable blade and to the stem of said piston, respectively, the lever being further connected to a chassis of the surgical device at a central position thereof.

5. A surgical device apt to the removal of bone, cartilaginous and the like tissues during surgery, comprising:
 a pair of side-by-side blades, slidably coupled so that respective distal ends thereof be closable the one against the other for the removal of a tissue fragment;
 propelling means, connected or connectible to a slidable blade of said pair and apt to determine the sliding thereof with respect to the other of said blades, said propelling means being pneumatic propelling means and comprising a piston having a stem apt to produce sliding of the slidable blade of said pair;
 operation means for the operation of said propelling means by a user;
 means for inhibiting operation of said propelling means; and
 a main body apt to be handled by a user and connected or connectible to said pair of blades, said main body comprising a portion apt to be handled by the user by a single hand, said operation means being located at said portion,
 wherein said piston is coupled to said slidable blade by interposition of a motion transmission member, said motion transmission member being a lever rotatably connected at opposed ends thereof to said slidable blade and to the stem of said piston, respectively, the lever being further connected to a chassis of the surgical device at a central position thereof.

6. A surgical device apt to the removal of bone, cartilaginous and the like tissues during surgery, comprising:
 a pair of side-by-side blades, slidably coupled so that respective distal ends thereof be closable the one against the other for the removal of a tissue fragment;
 propelling means, connected or connectible to a slidable blade of said pair and apt to determine the sliding thereof with respect to the other of said blades, said propelling means being pneumatic propelling means and comprising a piston having a stem apt to produce sliding of the slidable blade of said pair;
 operation means for the operation of said propelling means by a user;
 a main body apt to be handled by a user and connected or connectible to said pair of blades, said main body comprising a portion apt to be handled by the user by a single hand, said operation means being located at said portion; and
 means for preventing bone fragment entrapment between the blades of said pair,
 wherein said piston is coupled to said slidable blade by interposition of a motion transmission member, said motion transmission member being a lever rotatably connected at opposed ends thereof to said slidable blade and to the stem of said piston, respectively, the lever being further connected to a chassis of the surgical device at a central position thereof.

7. A surgical device apt to the removal of bone, cartilaginous and the like tissues during surgery, comprising:
 a pair of side-by-side blades, slidably coupled so that respective distal ends thereof be closable the one against the other for the removal of a tissue fragment;
 propelling means, connected or connectible to a slidable blade of said pair and apt to determine the sliding thereof with respect to the other of said blades, said propelling means being pneumatic propelling means and comprising a piston having a stem apt to produce sliding of the slidable blade of said pair;
 operation means for the operation of said propelling means by a user;
 a main body apt to be handled by a user and connected or connectible to said pair of blades, said main body comprising a portion apt to be handled by the user by a single hand, said operation means being located at said portion; and
 means for cooperating with a neuro-navigation system,
 wherein said piston is coupled to said slidable blade by interposition of a motion transmission member, said motion transmission member being a lever rotatably connected at opposed ends thereof to said slidable blade and to the stem of said piston, respectively, the lever being further connected to a chassis of the surgical device at a central position thereof.

8. The kit according to claim 1, comprising means for connecting with the pneumatic propelling means.

* * * * *

UNITED STATES PATENT AND TRADEMARK OFFICE
CERTIFICATE OF CORRECTION

| | | |
|---|---|---|
| PATENT NO. | : 7,850,694 B2 | Page 1 of 1 |
| APPLICATION NO. | : 10/551721 | |
| DATED | : December 14, 2010 | |
| INVENTOR(S) | : Laura Raus | |

It is certified that error appears in the above-identified patent and that said Letters Patent is hereby corrected as shown below:

Column 1, line 21, the word "rotabably" should read --rotatably--.

Column 1, line 37, the word "oseotomes" should read --osteotomes--.

Column 2, line 39, the word "bandied" should read --handled--.

Column 4, line 50, the word "operaton" should read --operation--.

Column 7, line 16, the word "neuronaviqation" should read --neuronavigation--.

Signed and Sealed this
Fifteenth Day of March, 2011

David J. Kappos
*Director of the United States Patent and Trademark Office*